(12) United States Patent
Jang

(10) Patent No.: US 7,390,323 B2
(45) Date of Patent: Jun. 24, 2008

(54) CATHETER

(75) Inventor: Yang-Soo Jang, Seoul (KR)

(73) Assignees: Humed Co., Ltd., Seoul (KR); Asahi Intecc Co., Ltd., Nagoya-Shi (JP)

( * ) Notice: Subject to any disclaimer, the term of this patent is extended or adjusted under 35 U.S.C. 154(b) by 0 days.

(21) Appl. No.: 11/350,400

(22) Filed: Feb. 8, 2006

(65) Prior Publication Data

US 2006/0184156 A1    Aug. 17, 2006

(30) Foreign Application Priority Data

Feb. 15, 2005    (JP) ............................. 2005-037481

(51) Int. Cl.
*A61M 25/01* (2006.01)
(52) U.S. Cl. .................. 604/528; 606/194; 604/264
(58) Field of Classification Search ................. 604/528, 604/43, 264; 606/108, 194; 623/1.35
See application file for complete search history.

(56) References Cited

U.S. PATENT DOCUMENTS

| | | | | |
|---|---|---|---|---|
| 5,135,535 | A | * | 8/1992 | Kramer ...................... 606/194 |
| 5,364,355 | A | * | 11/1994 | Alden et al. ............ 604/103.09 |
| 5,961,486 | A | | 10/1999 | Twardowski et al. |
| 6,045,557 | A | | 4/2000 | White et al. |
| 6,099,497 | A | | 8/2000 | Adams et al. |
| 6,129,738 | A | * | 10/2000 | Lashinski et al. ............ 606/194 |
| 6,165,195 | A | | 12/2000 | Wilson et al. |
| 6,440,161 | B1 | | 8/2002 | Madrid et al. |
| 6,682,536 | B2 | * | 1/2004 | Vardi et al. ................. 606/108 |
| 6,682,556 | B1 | | 1/2004 | Ischinger |
| 6,926,692 | B2 | | 8/2005 | Katoh et al. |
| 2004/0064128 | A1 | | 4/2004 | Raijman et al. |
| 2004/0073108 | A1 | | 4/2004 | Saeed et al. |
| 2004/0102719 | A1 | | 5/2004 | Keith et al. |
| 2004/0106866 | A1 | | 6/2004 | Ookubo et al. |
| 2004/0220473 | A1 | * | 11/2004 | Lualdi ........................ 600/435 |
| 2004/0249337 | A1 | * | 12/2004 | DiFiore ....................... 604/40 |

FOREIGN PATENT DOCUMENTS

| | | |
|---|---|---|
| JP | 2002-505148 A1 | 2/2002 |
| JP | 2004-267333 A1 | 9/2004 |
| WO | WO 99/44539 A1 | 9/1999 |
| WO | 03/068303 A2 | 8/2003 |

OTHER PUBLICATIONS

"Multifunctional Probing Catheter" Boston Scientific Scimed Catalog (w/ English Translation).

* cited by examiner

*Primary Examiner*—Nicholas D. Lucchesi
*Assistant Examiner*—Laura A Bouchelle
(74) *Attorney, Agent, or Firm*—Burr & Brown

(57) ABSTRACT

A catheter includes a main body; a first and a second lumen provided in the main body, wherein a first and a second guide wire are insertable in the first and second lumens, respectively; a first inclined surface provided, on a side of the center axis line, such that the first inclined surface is inclined frontward to approach the center axis line; a first opening formed in the first inclined surface and through which the first lumen opens outward; a second inclined surface provided, on the other side of the center axis line, such that the second inclined surface is inclined frontward to approach the center axis line; and a second opening formed in the second inclined surface and through which the second lumen opens outward.

22 Claims, 6 Drawing Sheets

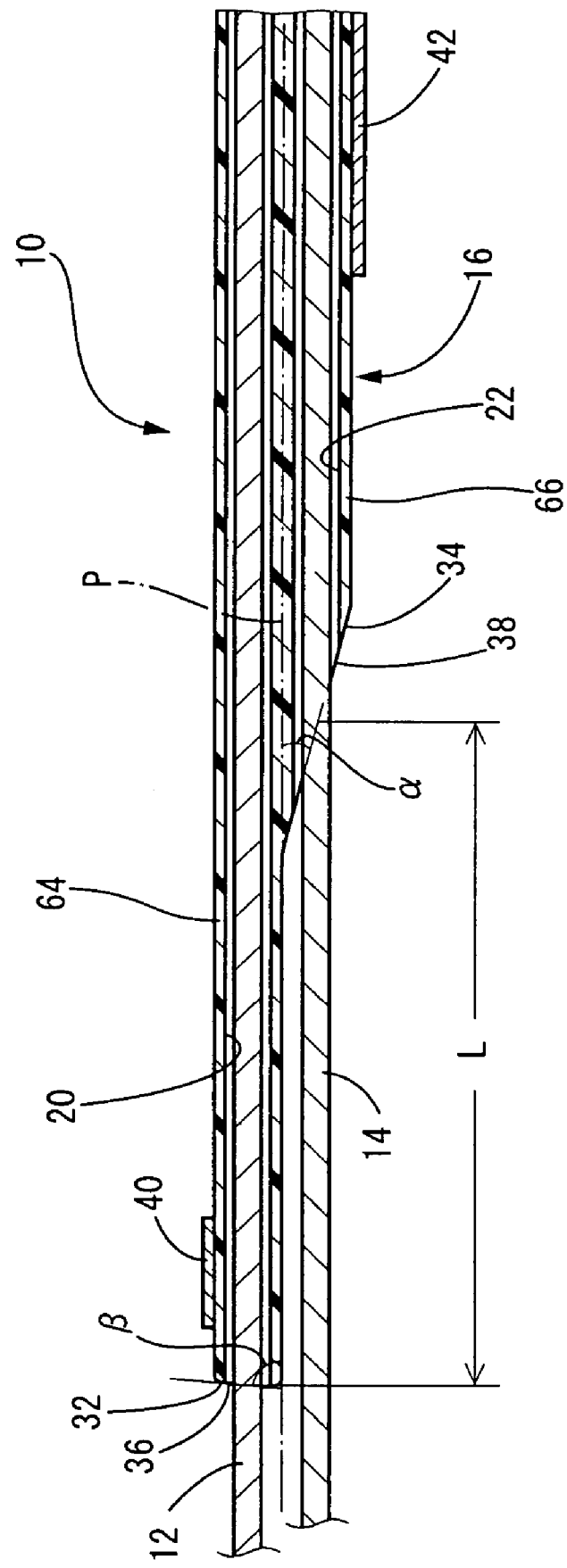

CATHETER

The present application is based on Japanese Patent Application No. 2005-037481 filed on Feb. 15, 2005, the contents of which are incorporated herein by reference.

BACKGROUND OF THE INVENTION

1. Field of the Invention

The present invention relates to a catheter and particularly to a novel structure of a catheter constructed such that two guide wires can be inserted therein or extended therethrough.

2. Discussion of Related Art

Conventionally, a catheter has been used as a sort of medical instrument that is inserted in a tubular organ of a human body, such as a blood vessel, a digestive tract, or a ureter, so as to carry out various treatments, examinations, or procedures. Generally, a catheter includes a main body that has a flexibility and is inserted in a human body. The main body of the catheter has a lumen that is formed therein and extends in an axial direction thereof. Since a guide wire that is inserted in a tubular organ of the human body is extended through the lumen of the main body, the main body can be inserted in the human body while being guided by the guide wire.

Each of Patent Document 1 (Japanese Patent Application Publication No. 2004-267333) and Patent Document 2 (Japanese Patent Application Publication No. 2002-505148) discloses a catheter that has the above-described structure and includes a main body in which two guide wires can be inserted. The main body of the catheter has two lumens formed therein and extending parallel to each other in an axial direction thereof. The two guide wires are inserted in the two lumens, respectively, such that a front end portion of each of the two guide wires projects frontward from a corresponding one of the two lumens and the each guide wire is movable in the axial direction. More specifically described, each guide wire may be inserted in the corresponding lumen in a so-called "monorail" manner in which the guide wire is inserted in the lumen through an opening formed in an outer circumferential surface of an axially intermediate portion of the main body, and is caused to project outward from an opening formed in a front end of the main body as seen in an insertion direction in which the main body is inserted in the human body, or in a so-called "over-the-wire" manner in which the guide wire is inserted in the lumen through an opening formed in a rear end surface of the main body as seen in the insertion direction, and is caused to project outward from an opening formed in the front end of the main body.

The above-indicated so-called "double-guide-wire" catheter through which two guide wires can be extended can find various applications. For example, in a state in which the main body of the catheter is inserted in a blood vessel having a total occlusion lesion, the two guide wires are moved forward in the two lumens, respectively, and respective front end portions of the two guide wires that project frontward from the main body are operated to pass through through the lesion and thereby treat the same.

SUMMARY OF THE INVENTION

However, generally, the conventional double-guide-wire catheter has a front end surface defined by a flat surface extending perpendicularly to the axial direction. In addition, the two lumens have the respective front openings formed in the front end surface and accordingly have respective shapes in a limited size corresponding to respective transverse cross-section shapes of the two lumens, taken along a plane extending perpendicularly to the axial direction. The two guide wires that are inserted in the two lumens, respectively, are caused to project outward through the two front openings, respectively, in the axial direction of the main body in which the lumens are formed. Thus, the conventional catheter has such a difficulty to advance freely the front end portion of each guide wire that projects frontward from the main body in a wider range of directions other than the axial direction of the main body when the each guide wire is externally operated by an operator.

Thus, when the conventional catheter and the two guide wires are used to treat, e.g., respective total occlusion lesions occurring to two branch blood vessels, it is not easy to insert the respective front end portions of the two guide wires into the two branch blood vessels, if an angle contained by the two blood vessels is large. In addition, when the catheter and the two guide wires are used to treat a total occlusion lesion occurring to a single blood vessel, it is difficult to carry out such a special treatment that in a state in which the front end portion of one of the two guide wires is inserted in the wall of the blood vessel, the front end portion of the other guide wire is advanced toward a target portion of the lesion of the blood vessel.

It is therefore an object of the present invention to provide a catheter having two lumens in which two guide wires can be inserted, respectively, such that each of the guide wires is movable in an axial direction of the catheter, and having an improved structure in which a front end portion of the each guide wire that projects frontward from a front end of the catheter as seen in a direction in which the catheter is inserted in a living being can be advanced freely in a wider range of directions, when the each guide wire is operated.

The Inventor has carried out extensive studies to achieve the above-indicated object, and has found that the object can be achieved by forming the respective front openings of the two lumens in respective inclined surfaces formed in a front end portion of a main body of the catheter.

(1) According to a first feature of the present invention, there is provided a catheter comprising: a main body insertable in a tubular organ of a living being, having a first lumen and second lumen, the first lumen provided for a first guide wire movably insertable in the first lumen, the second lumen provided for a second guide wire movably insertable in the second lumen, a first inclined surface formed in a front end portion of the main body on one side of an axis line of the main body, inclined toward the axis line of the main body in an insert direction of the main body into the tubular organ, the first inclined surface having a first opening, the first opening connected to the first lumen to permit the first guide wire to extend from the main body, a second inclined surface formed in the front end portion of the main body on the other side of the axis line of the main body, inclined toward the axis line of the main body in the insert direction of the main body into the tubular organ, the second inclined surface having a second opening, and the second opening connected to the second lumen to permit the second guide wire to extend from the main body.

Unlike the conventional catheter having the respective front openings formed in the flat surface perpendicularly to the axial direction of the main body, the catheter in accordance with the present invention has the first and second openings of the first and second lumens that can have respective shapes different from respective transverse cross-section shapes of the first and second lumens, taken along the plane extending perpendicularly to the axial direction of the main body, and accordingly can have respective areas larger than respective transverse cross-section areas of the first and second lumens.

In addition, in preferable case that the angle of inclination of the second inclined surface is smaller than that of the first inclined surface, the second opening can have a still larger area or size than that of the first opening.

Therefore, the catheter in accordance with the present invention assures that when each of the first and second guide wires is operated to move forward in a state in which the two guide wires are inserted in the two lumens, respectively, the front end portion of the each guide wire that projects from a corresponding one of the first and second openings can be freely advanced in a wider range of directions because of the larger size of the one opening.

In the preferable case, the range of directions in which the front end portion of the second guide wire that projects outward from the second opening can be advanced is more advantageously widened because of the still larger size of the second opening.

Thus, when the present catheter is used to treat, e.g., respective total occlusion lesions occurring to two branch blood vessels or a total occlusion lesion occurring to a single blood vessel, respective directions in which the respective front end portions of the first and second guide wires can be advanced in the blood vessels or vessel are more freely and smoothly controlled. Thus, the present catheter can be more easily operated to carry out the treatment.

(2) According to a second feature of the present invention, that may be combined with the first feature (1), the axis line of the main body is a center axis line of the main body.

(3) According to a third feature of the present invention that may be combined with the first or second feature (1) or (2), wherein an angle of inclination of the second inclined surface to the axis line of the main body is smaller than an angle of inclination of the first inclined surface to the axis line of the main body.

(4) According to a fourth feature of the present invention that may be combined with any of the first through third features (1) through (3), a length of the first opening along an angle of inclination of the first inclined surface to the axis line of the main body is longer than a diameter of the first lumen.

(5) According to a fifth feature of the present invention that may be combined with any of the first through fourth features (1) through (4), a length of the second opening along an angle of inclination of the second inclined surface to the axis line of the main body is longer than a diameter of the second lumen.

(6) According to a sixth feature of the present invention that may be combined with any one of the first through fifth features (1) through (5), the main body has a third opening in an outer circumferential surface between the front end portion and a rear end portion of the main body, which is connected to the first lumen to permit the first guide wire to extend from the main body.

(7) According to a seventh feature of the present invention that may be combined with the fifth feature (5), the main body has a forth opening in the rear end portion of the main body, which is connected to the second lumen to permit the second guide wire to extend from the main body.

(8) According to an eighth feature of the present invention that may be combined with the fifth feature (5), the catheter further comprising a holding portion attached on the main body to hold the first guide wire extended from the third opening.

(9) According to a ninth feature of the present invention that may be combined with any one of the first through eighth features (1) through (8), an angle of inclination of the first inclined surface to the axis line of the main body is 17 degrees or larger but smaller than 90 degrees.

(10) According to a tenth feature of the present invention that may be combined with any one of the first through ninth features (1) through (9), an angle of inclination of the second inclined surface to the axis line of the main body is between 14 and 60 degrees.

(11) According to an eleventh feature of the present invention that may be combined with any one of the first through tenth features (1) through (10), the front end portion of the main body has a stepped shape configured to position the first opening and the second opening apart from each other in a direction of the axis line of the main body.

(12) According to a twelfth feature of the present invention that may be combined with the eleventh feature (11), a distance between the first opening and the second opening is 10 mm or smaller.

(13) According to a thirteenth feature of the present invention that may be combined with any one of the first through twelfth features (1) through (12), the catheter further comprising a first marker portion provided adjacent to one of the first inclined surface and the second inclined surface in the main body and having a radiopaque characteristics configured to indicate one side of sides where the first inclined surface and the second inclined surface are respectively formed and to show a first length in a direction of the axis line of the main body.

(14) According to a fourteenth feature of the present invention that may be combined with the thirteenth (13), the catheter further comprising a second marker portion provided in rear of the first marker portion in the direction of the axis line, located apart from the first marker portion with a predetermined length, and which having a radiopaque characteristics configured to indicate the other side of the side where the first marker portion is provided and to show a second length in the direction of the axis line which is different from the first length.

BRIEF DESCRIPTION OF THE DRAWINGS

The above and other objects, features, advantages and technical and industrial significance of the present invention will be better understood by reading the following detailed description of presently preferred embodiments of the invention, when considered in connection with the accompanying drawings, in which:

FIG. 6 is an enlarged, cross-sectional view of a portion of another catheter as a second embodiment of the present invention.

DETAILED DESCRIPTION OF THE PREFERRED EMBODIMENTS

Hereinafter, there will be described in detail preferred embodiments of the present invention by reference to the drawings.

Figure 1:
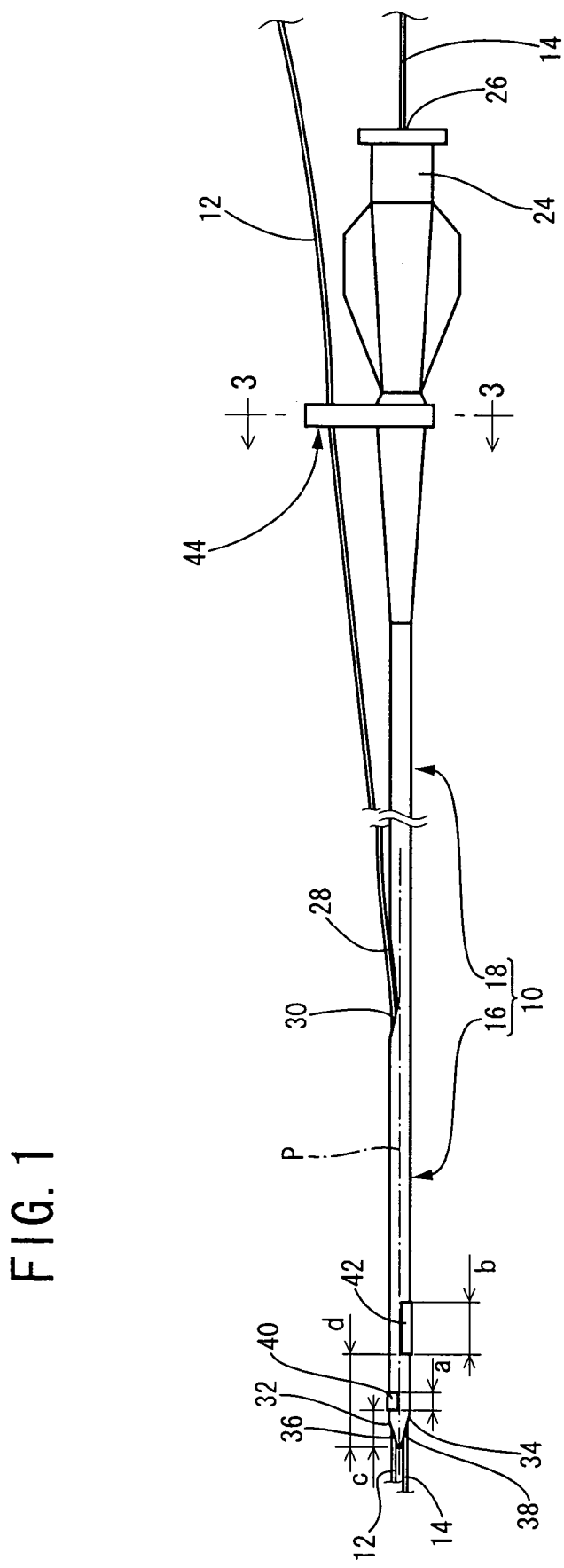
FIG. 1 is a front elevational view for explaining a structure of a catheter according to the present invention.

FIG. 1 shows, as a first embodiment, a catheter having a structure in accordance with the present invention. This catheter is used to treat a total occlusion lesion occurring to a blood vessel present in a surface of the cardiac muscle of a human being. The catheter is shown in a state in which two guide wires 12, 14 are inserted therein. As is apparent from FIG. 1, the present catheter includes a main body 10 (hereinafter, referred to as the "catheter main body", if appropriate) that is constituted by an elongate, cylindrical or tubular member. The first and second guide wires 12, 14 are inserted in the catheter main body 10, such that each of the two guide wires 12, 14 is movable in an axial direction of the main body 10 that is parallel to a center axis line P of the same 10.

More specifically described, the catheter main body 10 has a thickness and a length that assures that an entire length of the main body 10 can be inserted in a blood vessel of the human body that extends from a femoral portion or a wrist portion to the heart. The main body 10 is formed of a polyethylene resin. Thus, the main body 10 has a sufficiently high degree of flexibility and an appropriate degree of stiffness that are well balanced with each other, and accordingly it can be smoothly inserted in the winding blood vessel. However, the main body 10 may be formed of any known material that has conventionally been used to form main bodies of conventional catheters, so long as the material can give an adequate flexibility to the main body 10.

Figure 2:
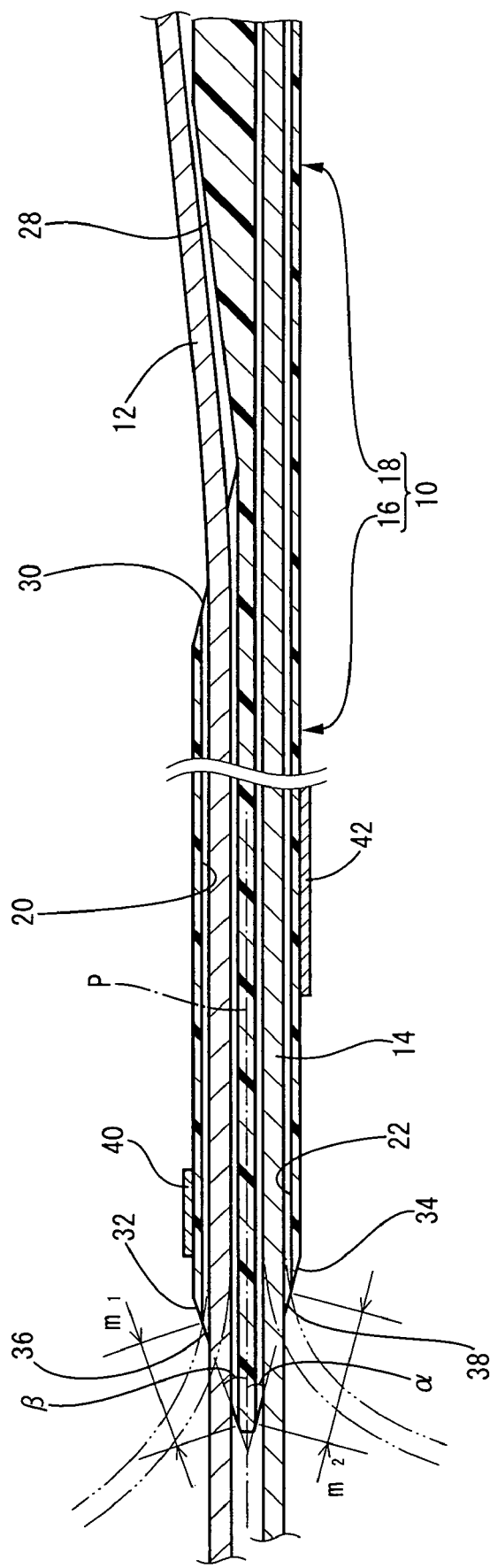
FIG. 2 is an enlarged, cross-sectional view of a portion of the catheter.

In addition, as is apparent from FIGS. 1 and 2, the catheter main body 10 includes a first main portion 16 that is provided by a front-side end portion of the main body 10 (i.e., a left-side end portion of the main body 10 in FIGS. 1 and 2) as seen in an insertion direction in which the main body 10 is inserted in the blood vessel of the human body. The first main portion 16 has a length of, e.g., about 17 cm. The main body 10 additionally includes a second main portion 18 that is provided by a remaining, major portion of the main body 10 that is located in rear of the first main portion 16 (i.e., on a right side of the first main portion 16 in FIGS. 1 and 2) as seen in the insertion direction. Each of the first and second main portions 16, 18 has an outer diameter of, e.g., about 1 mm. For the purpose of easier understanding of the structure of the catheter main body 10 or the catheter as a whole, the first and second main portions 16, 18 of the main body 10 will be referred to as the front-side and rear-side portions 16, 18 of the main body 10, if appropriate.

The first or front-side main portion 16 of the main body 10 has a first lumen 20 and a second lumen 22 that are formed therein such that the two lumens 20, 22 continuously extend parallel to each other in the axial direction of the main body 10 and are located at respective positions that are offset from the center axis line P of the main body 10 and are diametrically opposite to each other with respect to the axis line P. Meanwhile, the second or rear-side main portion 18 has an extension portion of the second lumen 22 that is continuous with the second lumen 22 in the first main portion 16 and continuously extends in the axial direction. Thus, in the present embodiment, the second lumen 22 is so formed as to extend over the entire length of the main body 10, and the first lumen 20 is so formed as to extend in only the first main portion 16, i.e., the front-side main portion 16.

A connector 24 is connected to a rear end of the second main portion 18. The connector 24 has a communication hole, not shown, that is formed therethrough such that the communication hole communicates with the second lumen 22 of the second main portion 18 and opens rearward through a rear opening 26 formed in a rear end surface of the connector 24. Thus, the second lumen 22 opens rearward through the rear opening 26 of the connector 24. In the present embodiment, the rear opening 26 of the connector 24 provides a fourth opening of the catheter.

The catheter main body 10 includes, in a boundary portion thereof between the first and second main portions 16, 18, a recessed portion that has a V-shaped configuration with a predetermined length in the axial direction and is formed in an outer circumferential surface thereof located on one side of the center axis line P, where the first lumen 20 is formed. The recessed portion has two inclined surfaces one of which provides an inclined guide surface 28 that is located on the side of the rear-side main portion 18 and is inclined frontward and downward. The other inclined surface of the recessed portion, located on the side of the front-side main portion 16, has an insertion hole 30 as a third opening through which the first lumen 20 opens rearward.

In the catheter main body 10 constructed as described above, the first guide wire 12 is inserted into the insertion hole 30 while being guided by the inclined guide surface 28 formed in the outer circumferential surface of the boundary portion between the first and second main portions 16, 18, and is further inserted, through the insertion hole 30, into the first lumen 20 continuously extending in the first main portion 16 in the axial direction, such that the first guide wire 12 is movable in the axial direction. In addition, the second guide wire 14 is inserted into the rear opening 26 of the connector 24 connected to the rear end of the second main portion 18, and is further inserted, through the communication hole of the connector 24, into the second lumen 22 continuously extending in the first and second main portions 16, 18 in the axial direction, such that the second guide wire 14 is movable in the axial direction.

In the present embodiment, the first main portion 16 has, in a front end portion thereof, a first inclined surface 32 and a second inclined surface 34; and a first opening 36 and a second opening 38 through which the first lumen 20 and the second lumen 22 open frontward, respectively, are formed in the first inclined surface 32 and the second inclined surface 34, respectively.

FIG. 2 shows a state in which the catheter main body 10 takes a horizontal posture in which the first lumen 20 is located on an upper side of the center axis line P and the second lumen 22 is located on a lower side of the same P. The first main portion 16 has such a shape that an upper, substantially half portion of the front end portion thereof, located on the upper side of the axis line P, and a lower, substantially half portion of the front end portion thereof, located on the lower side of the axis line P, are each obliquely cross-sectioned. Thus, the first main portion 16 has, in the front end portion thereof, the first inclined surface 32 formed by a cut surface of the frond end of the upper half portion where the first lumen 20 is formed, such that the first inclined surface 32 is inclined frontward to approach the center axis line P. The first main portion 16 additionally has the second inclined surface 34 formed by a cut surface of the front end of the lower half portion where the second lumen 22 is formed, such that the second inclined surface 34 is inclined frontward to approach the axis line P.

Since the first inclined surface 32 is defined by the beveled cut surface of the upper half portion of the front end portion of the first main portion 16 where the first lumen 20 is formed, the first opening 36 through which the first lumen 20 opens frontward is formed in a central portion of the first inclined surface 32, such that the first opening 36 has an elliptic shape whose major axis extends along the inclination direction of the first inclined surface 32. Likewise, since the second inclined surface 34 is defined by the beveled cut surface of the lower half portion of the front end portion of the first main portion 16 where the second lumen 22 is formed, the second opening 38 through which the second lumen 22 opens frontward is formed in a central portion of the second inclined surface 34, such that the second opening 38 has an elliptic shape whose major axis extends along the inclination direction of the second inclined surface 34.

Thus, unlike a comparative case where a front end surface of the first main portion 16 is defined by a flat surface extending perpendicularly to the center axis line P and two circular openings through which the first and second lumens 20, 22 open frontward, respectively, are formed in the flat, front end surface, each of a length $m_1$ of the major axis of the first opening 36 and a length $m_2$ of the major axis of the second opening 38, shown in FIG. 2, is sufficiently longer than a length (i.e., an internal diameter) of a corresponding one of the two circular openings.

In addition, in the present embodiment, an angle $\alpha$ of inclination of the second inclined surface 34 relative to the center axis line P (i.e., an angle contained by the second inclined surface 34 and the axis line P) is smaller than an angle $\beta$ of inclination of the first inclined surface 32 relative to the axis line P (i.e., an angle contained by the first inclined surface 32 and the axis line P), that is $\alpha<\beta$. Therefore, an area of the second inclined surface 34 is larger than an area of the first inclined surface 32. In addition, the length $m_2$ of the major axis of the second elliptic opening 38 is greater than the length $m_1$ of the major axis of the first elliptic opening 36. Thus, the second opening 38 has an overall size larger than that of the first opening 36.

The first guide wire 12 is inserted in the first lumen 20, and is caused to project frontward through the first opening 36. The second guide wire 14 is inserted in the second lumen 22, and is caused to project frontward through the second opening 38 larger than the first opening 36. In the present embodiment, the first guide wire 12 is inserted in the first lumen 20 in the "monorail" manner, and the second guide wire 14 is inserted in the second lumen 22 in the "over-the-wire" manner.

Therefore, as compared with the above-indicated case where the two circular openings are formed in the flat front end surface of the first main portion 16, a front end portion of the first guide wire 12 inserted in the present catheter can be caused to project, as indicated at two-dot chain lines in FIG. 2, through the first opening 36, in a lateral direction opposite to the second guide wire 14 (i.e., in an upward direction in FIG. 2), so that the front end portion of the first guide wire 12 can be ranged with a greater angle or can be curved with a smaller radius of curvature.

In addition, the second guide wire 14 is inserted in the main body 10 of the catheter in the "over-the-wire" manner, and the second opening 38 has the still larger size than that of the first opening 36. Therefore, as indicated at two-dot chain lines in FIG. 2, a front end portion of the second guide wire 14 can be caused to project through the second opening 38 in a lateral direction opposite to the first guide wire 12 (i.e., in a downward direction in FIG. 2), while receiving a great back-up force based on support of the second lumen 22 so that the front end portion of the second guide wire 14 can be ranged with a still greater angle or can be curved with a still smaller radius of curvature.

The inclination angle $\beta$ of the first inclined surface 32 and the inclination angle $\alpha$ of the second inclined surface 34 are not limited to any specific angles, but preferably the latter angle $\alpha$ is smaller than the former angle $\beta$. However, it is preferred that the inclination angle $\beta$ of the first inclined surface 32 is 17 degrees or larger but is smaller than 90 degrees. The inclination angle $\alpha$ of the second inclined surface 34 is between 14 and 60 degrees.

If the respective inclination angles $\beta$, $\alpha$ of the first and second inclined surfaces 32, 34 are smaller than the above-indicated respective lower limits, those inclination angles $\beta$, $\alpha$ are too small and accordingly the front end portion of the catheter main body 10 becomes too sharp. On the other hand, if the inclination angle $\beta$ of the first inclined surface 32 is equal to 90 degrees, the first surface 32 cannot form as an inclined surface relative to the center axis line P so that the first opening 36 formed in the first surface 32 has the same size (i.e., the same diameter) as that of each of the above-described two circular openings. In addition, if the inclination angle $\alpha$ of the second inclined surface 34 is greater than the above-indicated upper limit, the area of the second opening 38 cannot be sufficiently increased by having the second surface 34 inclined, and accordingly the respective curving or ranging amounts in the opposite lateral directions of the respective front end portions of the first and second guide wires 12, 14 cannot be sufficiently increased.

Thus, in the present catheter, since the inclination angle $\beta$ of the first inclined surface 32 is not smaller than 17 degrees and is smaller than 90 degrees and the inclination angle $\alpha$ of the second inclined surface 34 is between 14 and 60 degrees, the main body 10 can be smoothly inserted in the blood vessel, and a range of directions in which each of the first and second guide wires 12, 14 is allowed to project from a corresponding one of the first and second openings 36, 38 can be advantageously widened.

In addition, as shown in FIG. 1, a first marker portion 40 and a second marker portion 42 are fixed to an outer circumferential surface of the front end portion of the first main portion 16 of the catheter main body 10. Each of the first and second marker portions 40, 42 is constituted by a hemi-cylindrical member formed of a radiopaque material such as gold, platinum, or platinum-rhodium alloy. A hemi-cylindrical member may be obtained by cutting a full-cylindrical member by a plane containing a center axis line thereof. A length a of the first marker portion 40 constituted by the hemi-cylindrical member is e.g., about 1 mm; and a length b of the second marker portion 42 is sufficiently longer than the length a of the first marker portion 40 and is e.g., about 3 mm.

The first marker portion 40 is fixed to the outer circumferential surface of the front end portion of the first main portion 16, such that the first marker portion 40 is located in rear of, and in vicinity of, the first inclined surface 32 and covers an upper half portion of the outer circumferential surface that is located on the upper side of the center axis line P where the first inclined surface 32 is formed. In addition, the second marker portion 42 is fixed to the outer circumferential surface of the front end portion of the first main portion 16, such that the second marker portion 42 is located in rear of the first marker portion 40 and covers a lower half portion of the outer circumferential surface that is located on the lower side of the axis line P where the second inclined surface 34 is formed. In the present embodiment, a distance c between the front end of the first main portion 16 and a front end of the first marker portion 40 is e.g., about 2 mm and a distance d between the front end of the first main portion 16 and a front end of the second marker portion 42 is e.g., about 5 mm. Therefore, a distance d-c-a between a rear end of the first marker portion 40 and the front end of the second marker portion 42 is e.g., about 2 mm.

When the main body 10 of the present catheter is inserted in a blood vessel of the human body, respective positions of each of the short first marker portion 40 and the long second marker portion 42 in the blood vessel in the axial and the circumferential directions thereof can be recognized under radioscopy by an operator, and accordingly respective positions of the first and second openings 36, 38 in the blood vessel in the axial and the circumferential directions can be easily recognized by the operator. Therefore, respective projecting positions and directions in the blood vessel of the respective front end portions of the first and second guide wires 12, 14 can be easily known. In the present embodiment, since the respective lengths a, b of the first and second marker portions 40, 42 and the distance (d-c-a) between the two marker portions 40, 42 are selected at the above-indicated dimensions, the two marker portions 40, 42 can be reliably distinguished from each other under radioscopy.

Figure 3:
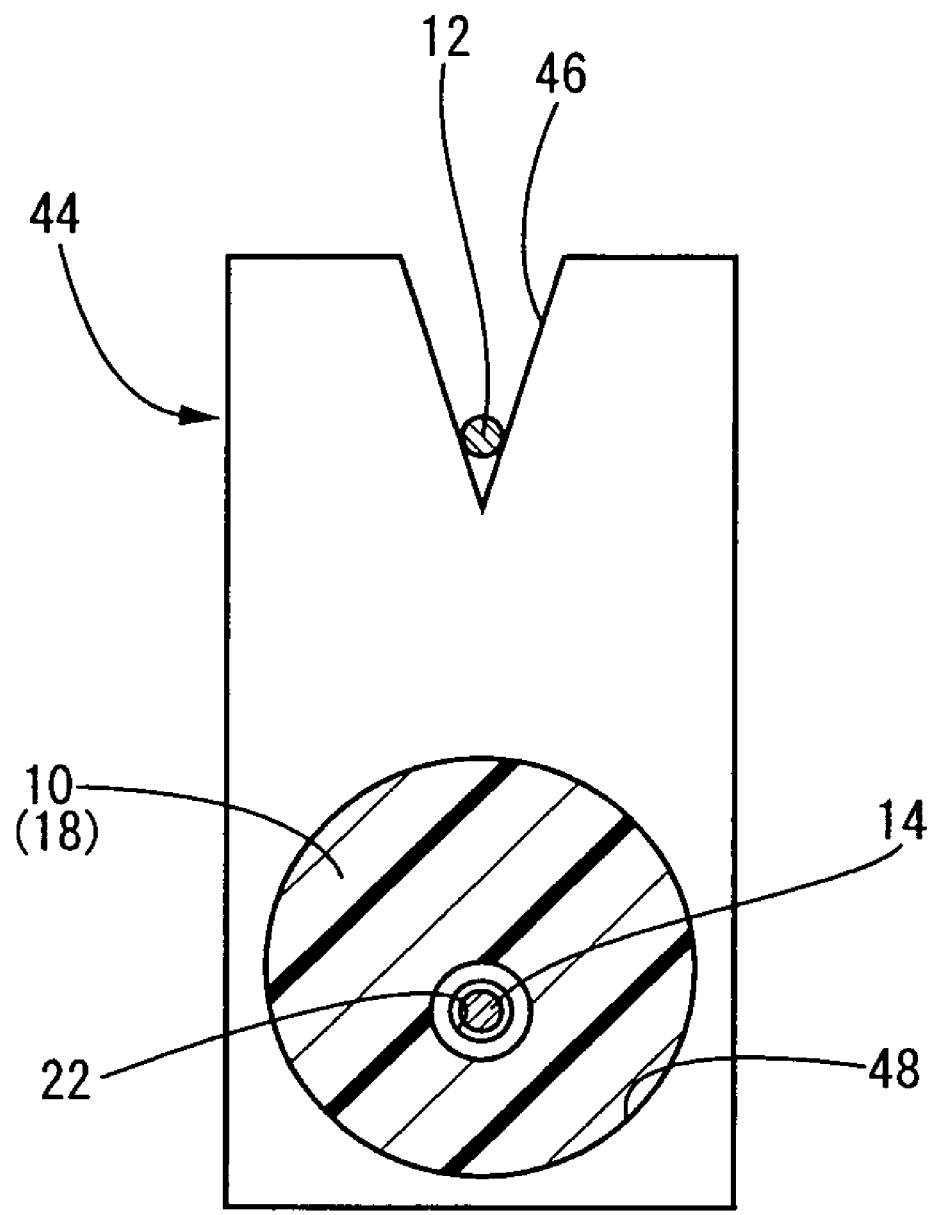
FIG. 3 is an enlarged, cross-sectional view of the catheter, taken along 3-3 in FIG. 1.

As shown in FIG. 1, the present catheter additionally includes a holding portion 44 that is attached to a rear end portion of the second main portion 18. As is apparent from FIGS. 1 and 3, the holding portion 44 is constituted by a flat plate member having an elongate rectangular shape and has a V-shaped groove 46 having a predetermined depth in a central portion of one of lengthwise opposite end surfaces thereof. The holding portion 44 has an attachment hole 48 formed through a thickness thereof in the other end portion thereof.

The holding portion 44 is attached to the rear end portion of the second main portion 18, such that the holding portion 44 fits on the rear end portion, i.e., the rear end portion extends through the attachment hole 48 of the holding portion 44. In a state in which the catheter main body 10 is inserted in the blood vessel of the human body, the rear end portion of the second main portion 18 remains outside the human body. In addition, in a state in which the first guide wire 12 is inserted in the main body 10 (i.e., the first lumen 20 thereof), a rear end portion of the first guide wire 12 that projects rearward from the insertion hole 30 is sandwiched, and thereby held, by two inclined surfaces that cooperate with each other to define the V-shaped groove 46 of the holding portion 44 attached to the second main portion 18.

Thus, when the catheter main body 10 is inserted in the blood vessel in the state in which the first guide wire 12 is inserted in the main body 10 in the "monorail" manner, the first guide wire 12 can be held by the holding portion 44. Thus, a relative rotational displacement between the first guide wire 12 and the main body 10 can be prevented.

Thus, the main body 10 and the first guide wire 12 can be effectively prevented from being entangled with each other in the blood vessel, and accordingly the main body 10 can be easily drawn out of the human body in a state in which the first guide wire 12 is left in the human body.

In addition, the first guide wire 12 and the main body 10 are prevented from being rotated relative to each other, as described above. Therefore, after the front end portion of the main body 10 has reached the target position in the blood vessel, the front end portion of the first guide wire 12 that projects outward from the first opening 36 of the front end portion of the main body 10 can be reliably rotated in a desired circumferential direction of the main body 10 by rotating a rear portion of the main body 10 that remains outside the human body, such that an amount of rotation of the front end portion of the first guide wire 12 in the circumferential direction of the main body 10 corresponds to an amount of rotation of the rear portion of the main body 10 in the same direction. Thus, the main body 10 can enjoy an excellent ability of transmitting torque to the first guide wire 12.

Next, there will be described a method of treating with the present catheter respective total occlusion lesions occurring to a main blood vessel present in the surface of the cardiac muscle and a branch blood vessel of the main blood vessel, or a total occlusion lesion occurring to a main blood vessel only.

Figure 4:
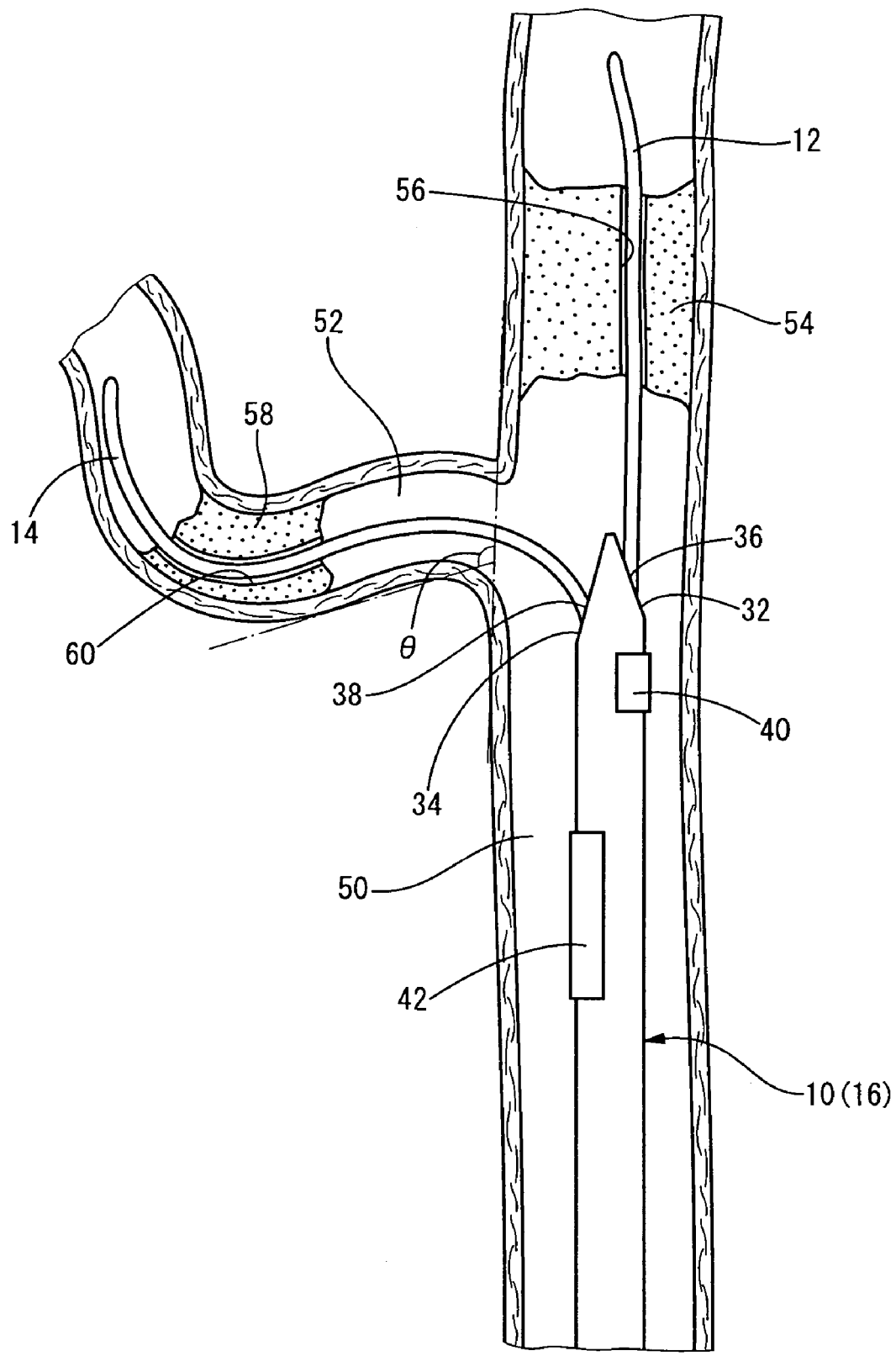
FIG. 4 is a view for explaining a manner in which the catheter is used, i.e., a view showing a state in which two guide wires are inserted in a main blood vessel and a branch blood vessel, respectively, so as to pass through respective total occlusion lesions of the two blood vessels.

First, the method in which the present catheter is used to treat the respective total occlusion lesions 54, 58 occurring to the main blood vessel 50 and the branch blood vessel 52 will be described by reference to FIG. 4. The main body 10 through which the two guide wires 12, 14 are extended is inserted in the main blood vessel 50 and is positioned in vicinity of a portion of the main blood vessel 50 where the branch blood vessel 52 is bifurcated, and in front of the total occlusion lesion 54 occurring to the main blood vessel 50. In FIG. 4, and also in FIG. 5, described later, blood flowing in the blood vessels 50, 52 is not shown for easier understanding purposes only.

Subsequently, the operator operates, outside the human body, the first guide wire 12 to move forward so that the front end portion of the first guide wire 12 that projects frontward from the first opening 36 advances toward the total occlusion lesion 54 of the main blood vessel 50. Eventually, the front end portion of the first guide wire 12 passes through the total occlusion lesion 54 of the main blood vessel 50 and thereby forms a through-hole 56 in the lesion 54. Thus, the blood is allowed to flow through the main blood vessel 50.

After, or before, the above-described operation, the operator operates, outside the human body, the second guide wire 14 to move forward so that the front end portion of the second guide wire 14 that projects frontward from the second opening 38 advances in a lateral direction opposite to the first guide wire 12, so that the front end portion of the second guide wire 14 enters the branch blood vessel 52.

As described above, in the present catheter, the front end portion of the second guide wire 14 can project, from the second opening 38, in the lateral direction (i.e., the leftward direction in FIG. 4) opposite to the first guide wire 12, while being bent by a still greater angle or curved with a still smaller radius of curvature. In addition, the second guide wire 14 is inserted in the main body 10 in the "over-the-wire" manner. Therefore, even if an angle $\Theta$ contained by the main blood vessel 50 and the branch blood vessel 52 may be considerably great, the front end portion of the second guide wire 14 can be very easily and smoothly inserted in the branch blood vessel 52, owing to the larger bending or curving of the front end portion of the second guide wire 14 and the greater backup force of the second lumen 22 given to the second guide wire 14.

After the front end portion of the second guide wire 14 is inserted in the branch blood vessel 52, the greater backup force of the second lumen 22 given to the second guide wire 14 helps the front end portion of the second guide wire 14 to pass through the total occlusion lesion 58 occurring to the branch blood vessel 52 and thereby form a through-hole 60 in the lesion 58. Thus, the blood is allowed to flow through the branch blood vessel 52.

Next, the method in which the present catheter is used to treat the total occlusion lesion 54 occurring to the main blood vessel 50 will be described by reference to FIG. 5. First, the main body 10 through which the two guide wires 12, 14 are extended is inserted in the main blood vessel 50 and is positioned in front of the total occlusion lesion 54 of the main blood vessel 50.

Subsequently, the operator operates, outside the human body, the first guide wire 12 to move forward so that the front end portion of the first guide wire 12 that projects frontward from the first opening 36 advances toward a wall 62 of the main blood vessel 50 while passing through the total occlusion lesion 54. Eventually, the front end portion of the first guide wire 12 is inserted into the blood-vessel wall 62, more specifically described, into a gap present between the endothelium and media of the wall 62.

Then, the operator operates, outside the human body, the second guide wire 14 to move forward so that the front end portion of the second guide wire 14 that projects frontward from the second opening 38 advances toward the total occlusion lesion 54. Eventually, the front end portion of the second guide wire 14 passes through the total occlusion lesion 54 and thereby forms the through-hole 56 in the lesion 54, and accordingly the blood is allowed to flow through the main blood vessel 50.

Figure 5:
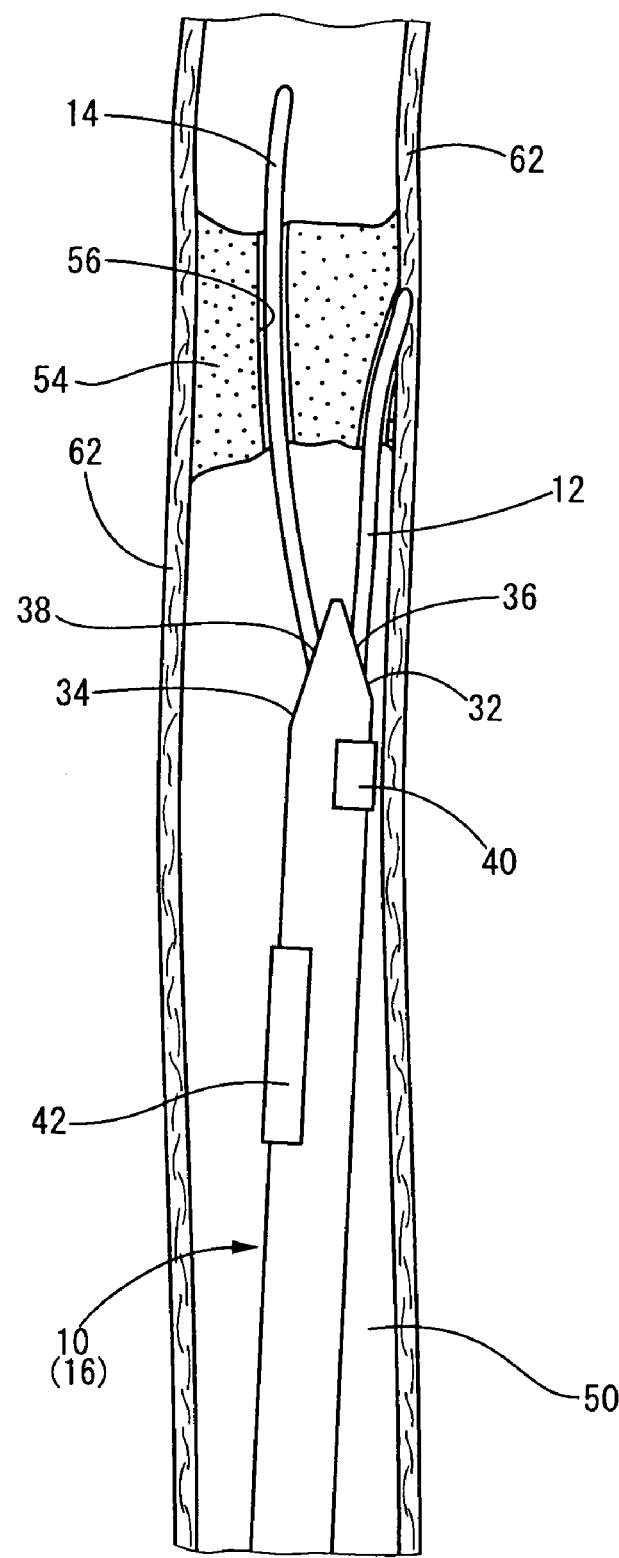
FIG. 5 is a view for explaining another manner in which the catheter is used, i.e., a view showing a state in which two guide wires are both inserted in a single blood vessel, so as to pass through a total occlusion lesion of the blood vessel.

Even if, as shown in FIG. 5, in order to carry out the sensitive operation of inserting the front end portion of the first guide wire 12 into the blood-vessel wall 62, the catheter main body 10 may be inclined toward the wall 62, the front end portion of the second guide wire 14 can be very easily and smoothly operated to pass through the total occlusion lesion 54 owing to the larger bending or curving of the front end portion of the second guide wire 14 and the greater backup force of the second lumen 22 given to the second guide wire 14.

When the total occlusion lesion 54 of the main blood vessel 50 and/or the total occlusion lesion 58 of the branch blood vessel 52 are/is treated, the catheter main body 10 may be operated, as needed, to enlarge the through-holes 56, 60 after the respective front end portions of the first and second guide wires 12, 14 are operated to pass through the respective total occlusion lesions 54, 58. In addition, subsequently, the present catheter may be replaced with another catheter, as needed, so as to enlarge further each through-hole 56, 60, and/or a stent may be provided, if appropriate.

As is apparent from the foregoing description of the present catheter, in the state in which the main body 10 in which the first and second guide wires 12, 14 are inserted in the first and second lumens 20, 22 thereof, respectively, is inserted in the main blood vessel 50, each of the two guide wires 12, 14 can be operated to move forward such that the direction of advancement of the front end portion of the each guide wire 12, 14 can be easily controlled or changed in the wider angular range. Since the front end portion of the each guide wire 12, 14 thus controlled is used to pass through the total occlusion lesion 54, 58 occurring to the main or branch blood vessel 50, 52, the operation of causing the blood to flow in the main or branch blood vessel 50, 52 can be more smoothly carried out.

Thus, when the present catheter is used to treat the respective total occlusion lesions 54, 58 occurring to the main and branch blood vessels 50, 52 that contain the considerably great angle, or treat the total occlusion lesion 54 of the main blood vessel 50 in the state in which the front end portion of the first guide wire 12 is inserted in the wall 62 of the main blood vessel 50, those treatments can be very smoothly and easily carried out.

In addition, in the present embodiment, when the catheter main body 10 is inserted in the main blood vessel 50, the respective projecting positions, and respective projecting directions, of the respective front end portions of the first and second guide wires 12, 14 in the main or branch blood vessel 50, 52 can be easily recognized under radioscopy, as described above. Therefore, if the total occlusion lesion 54, 58 occurring to the main or branch blood vessel 50, 52 is treated under radioscopy, then those treatments can be more smoothly carried out.

Moreover, in the present embodiment, in the state in which the catheter main body 10 is inserted in the main blood vessel 50, the main body 10 can enjoy the sufficiently high ability of transmitting torque to the first guide wire 12. Therefore, when the total occlusion lesion 54 of the main blood vessel 50 is treated in the state in which the main body 10 is inserted in the main blood vessel 50, the operability of the first guide wire 12 can be more effectively improved, and accordingly the treatment of the total occlusion lesion 54 can be still more smoothly carried out.

FIG. 6 shows a portion of another catheter as a second embodiment of the present invention. The second catheter differs from the first catheter as the first embodiment, shown in FIGS. 1 and 2, in that a front end portion of a first main portion 16 of the second catheter has a shape different from that of the front end portion of the first main portion 16 of the first catheter. The same reference numerals as used in the first embodiment are used to designate the corresponding elements and parts of the second embodiment, and the detailed description thereof is omitted.

As is apparent from FIG. 6, a front end portion of a main body 10 (or the first main portion 16 thereof) of the second catheter has a stepped shape in which a substantially half portion of the front end portion where a first lumen 20 is formed projects frontward from a remaining half portion of the front end portion where a second lumen 22 is formed.

More specifically described, the half portion of the front end portion where the first lumen 20 is formed provides a projecting portion 64 that projects frontward from the remaining half portion of the front end portion where the second lumen 22 is formed; and the remaining half portion of the front end portion where the second lumen 22 is formed provides a non-projecting portion 66. A front end surface of the projecting portion 64 defines a first inclined surface 32 having a first opening 36; and a front end surface of the non-projecting portion 66 defines a second inclined surface 34 having a second opening 38.

In the front end portion of the catheter main body 10, the first opening 36 formed in the first inclined surface 32 is located apart frontward from the second opening 38 formed in the second inclined surface 34, by a predetermined distance L, e.g., about 10 mm. Therefore, from the front end of the projecting portion 64 located in the front-side portion of the main body 10, a first guide wire 12 inserted in the first lumen 20 can be caused to project in a lateral direction through the first opening 36, in a state in which the first guide wire 12 is bent or curved. In addition, from the front end of the non-projecting portion 66 located in the rear-side portion of the main body 10, a second guide wire 14 inserted in the second lumen 22 can be caused to project in an opposite lateral direction through the second opening 38, in a state in which the second guide wire 14 is bent or curved.

The above-indicated distance L between the first and second openings 36, 38 is not limited to any specific values. Preferably, the distance L is selected at a value about 10 mm or shorter. If the distance L is more than 10 mm, then the front end portion of the catheter main body 10 shows the excessively long projecting portion 64 whose diameter is considerably small and accordingly whose stiffness is considerably low. That is, the front end portion of the catheter main body 10 exhibits a low stiffness. In this case, when the main body 10 is moved forward in a blood vessel 50 the front end portion of the main body 10 may be locally and easily bent or deformed. This means that the main body 10 may be inhibited from being smoothly moved in the blood vessel 50.

In the second embodiment, an angle $\beta$ of inclination of the first inclined surface 32 is selected at a considerably great degree, e.g., about 85 degrees. In addition, a front end portion of the projecting portion 64 that defines the first inclined surface 32 has a convexly curved shape that is convex in a frontward direction. Thus, the front end portion of the projecting portion 64 enjoys a very smooth shape. Therefore, when the catheter main body 10 is inserted in the blood vessel 50 an inner surface of the blood vessel 50 can be prevented from being damaged by the front end portion of the projecting portion 64.

Thus, since the first and second openings 36, 38 from which the first and second guide wires 12, 14 are caused to project, respectively, are formed in the first and second inclined surfaces 32, 34 of the front end portion of the catheter main body 10, respectively, the second catheter can enjoy the same advantages as those of the first catheter.

In the second embodiment, from the front end of the projecting portion 64 located in the front-side portion of the front end portion of the catheter main body 10, and from the front end of the non-projecting portion 66 located in the rear-side portion of the front end portion of the main body 10, the first and second guide wires 12, 14 can be caused to project in the opposite lateral directions through the first and second openings 36, 38, respectively, as described above. Therefore, for example, when the main body 10 is rotated about the center axis line P, respective front end portions of the first and second guide wires 12, 14 that project outward from the main body 10 can be advantageously prevented from being entangled with each other. In addition, the respective front end portions of the first and second guide wires 12, 14 that project outward from the main body 10 can be reliably rotated in a desired circumferential direction of the main body 10 by rotating the rear portion of the main body 10 that remains outside the human body, such that respective amounts of rotation of the front end portions of the first and second guide wires 12, 14 in the circumferential direction of the main body 10 correspond to an amount of rotation of the rear portion of the main body 10 in the same direction. Thus, the main body 10 can enjoy a good ability of transmitting torque to the first and second guide wires 12, 14.

Thus, the second catheter can be advantageously used to treat the total occlusion lesion 54, 58 occurring to the main or branch blood vessel 50, 52.

While the present invention has been described in its preferred embodiments, it is to be understood that the present invention is by no means limited to the details of those embodiments but may be otherwise embodied.

For example, in each of the illustrated embodiments, the first guide wire 12 is inserted in the catheter main body 10 in the "monorail" manner. However, the first guide wire 12 may be inserted in the main body 10 in the "over-the-wire" manner. In the latter case, the insertion hole 30 as the rear opening of the first lumen 20 is replaced with an opening formed in the rear end surface of the main body 10.

In the case where the first guide wire 12 is inserted in the catheter main body 10 in the "over-the-wire" manner, the second guide wire 14 may be inserted in the main body 10 in the "monorail" manner.

In the catheter main body 10, there may be provided a needle-like tubular member for introducing, e.g., a medicinal liquid from outside the human body into an appropriate internal tissue of the human body. In addition, a balloon may be externally attached to the main body 10.

In the first embodiment, the holding portion 44 attached to the catheter main body 10 can hold the rear end portion of the first guide wire 12 that projects rearward from the main body 10 and remains outside the human body in the state in which the main body 10 is inserted in the human body. However, so long as the holding portion 44 has this function, the holding portion 44 may be modified to have a different structure or shape, or may provided at a different position or in a different number.

In the second embodiment, the first opening 36 is located apart frontward from the second opening 38. However, conversely, the second opening 38 may be located apart frontward from the first opening 36.

More specifically described, for example, the front end portion of the catheter main body 10 may be modified to include a projecting portion 64 in which a second inclined surface 34 is formed, and a non-projecting portion 66 in which a first inclined surface 32 is formed. In this case, the second opening 38 formed in the second inclined surface 34 is located apart frontward from the first opening 36 formed in the first inclined surface 32. In this case, when the main body 10 is rotated about the center axis line P, the respective front end portions of the first and second guide wires 12, 14 that project outward from the main body 10 can be advantageously prevented from being entangled with each other. This advantage can be obtained so long as the first and second openings 36, 38 are located apart from each other in the axial direction of the main body 10.

In each of the described embodiments, the principle of the present invention is applied to the catheter that is used to treat the total occlusion lesion occurring to the blood vessel present in the surface of the cardiac muscle. However, the present invention can be advantageously applied to any sort of catheter that is constructed such that two guide wires can be inserted therein or extended therethrough.

It is to be understood that the present invention may be embodied with other changes, modifications, and improvements that may occur to a person skilled in the art, without departing from the spirit and scope of the present invention.

What is claimed is:

1. A catheter comprising:
    a main body insertable in a tubular organ of a living being, the main body including first main portion and a second main portion, each of which having a substantially consistent outside diameter,
    the first main portion having a first lumen and a second lumen, the two lumens being located symmetrically on either side of a center axis line of the catheter, the first lumen provided for a first guide wire movably insertable in the first lumen, the second lumen provided for a second guide wire movably insertable in the second lumen, the second guide wire passing into the second lumen at a transition between the first main portion and the second main portion,
    a first inclined surface formed in a front end portion of the main body on one side of the center axis line of the main body, inclined toward the center axis line of the main body in an insert direction of the main body into the tubular organ, the first inclined surface having a first opening,
    the first opening connected to the first lumen to permit the first guide wire to extend from the main body,
    a second inclined surface formed in the front end portion of the main body on the other side of the axis line of the main body, inclined toward the axis line of the main body in the insert direction of the main body into the tubular organ, the second inclined surface having a second opening, and
    the second opening connected to the second lumen to permit the second guide wire to extend from the main body; and a first marker portion provided in the main body and having radiopaque characteristics configured to indicate a side where the first inclined surface is formed and to show a first predetermined length in a direction of the center axis line, and a second marker portion provided in the main body and having radiopaque characteristics to indicate a side where the second inclined surface is formed to show a second predetermined length in the direction of the axis line that is different from the first predetermined length, wherein an angle of inclination of the second inclined surface is smaller than an angle of inclination of the first inclined surface so that the second guide wire can extend from the second opening with a greater angle or a smaller radius of curvature than the first guide wire extending from the first opening.

2. The catheter according to claim 1, wherein a length of the first opening along an angle of inclination of the first inclined surface to the axis line of the main body is longer than a diameter of the first lumen.

3. The catheter according to claim 1, wherein a length of the second opening along an angle of inclination of the second inclined surface to the axis line of the main body is longer than a diameter of the second lumen.

4. The catheter according to claim 1, wherein the main body has a third opening in an outer circumferential surface between the front end portion and a rear end portion of the main body, which is connected to the first lumen to permit the first guide wire to extend from the main body.

5. The catheter according to claim 3, wherein the main body has a fourth opening in the rear end portion of the main body, which is connected to the second lumen to permit the second guide wire to extend from the main body.

6. The catheter according to claim 3, the catheter further comprising a holding portion attached on the main body to hold the first guide wire extended from the third opening.

7. The catheter according to claim 1, wherein an angle of inclination of the first inclined surface to the axis line of the main body is 17 degrees or larger but smaller than 90 degrees.

8. The catheter according to claim 1, wherein an angle of inclination of the second inclined surface to the axis line of the main body is between 14 and 60 degrees.

9. The catheter according to claim 1, wherein the front end portion of the main body has a stepped shape configured to position the first opening and the second opening apart from each other in a direction of the axis line of the main body.

10. The catheter according to claim 9, wherein a distance between the first opening and the second opening is 10 mm or smaller.

11. The catheter according to claim 1, wherein the second marker portion is provided in rear of the first marker portion in the direction of the axis line, located apart from the first marker portion.

12. A catheter comprising:
a main body which is insertable in a tubular organ of a living being, the main body including a first main portion and a second main portion, each of which having a substantially consistent outside diameter;
a first lumen and a second lumen which are provided in the first main portion of the main body, on either side of a center axis line of the catheter, such that the first and second lumens extend in an axial direction parallel to the center axis line, wherein a first guide wire is insertable in the first lumen such that the first guide wire is moveable in the axial direction, and a second guide wire passes into the second lumen at a transition between the first main portion and the second main portion such that the second guide wire is moveable in the axial direction;
a first inclined surface provided in the first main portion of the main body as seen in a direction in which the main body is inserted in the tubular organ, on one side of the center axis line on which side the first lumen is formed, such that the first inclined surface is inclined frontward to approach the center axis line;
a first opening formed in the first inclined surface and through which the first lumen opens outward and the first guide wire, inserted in the first lumen, is permitted to project outward;
a second inclined surface provided in the front end portion of the main body, on the other side of the center axis line on which side the second lumen is formed, such that the second inclined surface is inclined frontward to approach the center axis line, and an angle of inclination of the second inclined surface relative to the center axis line is smaller than an angle of inclination of the first inclined surface relative to the center axis line; and
a second opening which is formed in the second inclined surface and through which the second lumen opens outward and the second guide wire, inserted in the second lumen, is permitted to project outward;
a first marker portion provided in the main body and having radiopaque characteristics configured to indicate a side where the first inclined surface is formed and to show a first predetermined length in a direction of the center axis line, and a second marker portion provided in the main body and having radiopaque characteristics to indicate a side where the second inclined surface is formed and to show a second predetermined length in the direction of the axis line that is different from the first predetermined length,
wherein the second guide wire can project outward from the second opening with a greater angle or smaller radius of curvature than the first guide wire can project outward from the first opening.

13. The catheter according to claim 12, wherein the main body has a third opening in an outer circumferential surface thereof through which the first lumen opens outward and the first guide wire is insertable in the first lumen such that the first guide wire is movable in the axial direction, and wherein the main body has a fourth opening in a rear end surface thereof as seen in the direction in which the main body is inserted in the tubular organ through which the second lumen opens outward and the second guide wire is insertable in the second lumen such that the second guide wire is movable in the axial direction.

14. The catheter according to claim 13, wherein the main body includes a holding portion, in a rear end portion thereof as seen in the direction in which the main body is inserted in the tubular organ, a not-to-be-inserted portion which is not to be inserted in the tubular organ, which holds a projecting portion of the first guide wire that projects outward through the third opening in a state in which the first guide wire is inserted in the first lumen through the third opening, such that the projecting portion is not rotatable relative to the main body.

15. The catheter according to claim 12, wherein the angle of inclination of the first inclined surface relative to the center axis line is not smaller than 17 degrees and is smaller than 90 degrees, and the angle of inclination of the second inclined surface relative to the center axis line is between 14 and 60 degrees.

16. The catheter according to claim 12, wherein the front end portion of the main body as seen in the direction in which the main body is inserted in the tubular organ has a stepped shape in which one of a first portion of the front end portion in which the first inclined surface is formed and a second portion of the front end portion in which the second inclined surface is formed projects frontward from the other of the first and second portions, so that the first and second openings are located apart from each other in the axial direction of the main body.

17. The catheter according to claim 16, wherein a distance by which the first and second openings are apart from each other is 10 mm or smaller.

18. The catheter according to claim 12, wherein the first marker portion is fixedly provided in a first portion of the main body that is located in rear of the first inclined surface as seen in the direction in which the main body is inserted in the tubular organ, and on said one side of the center axis line on which side the first lumen is formed, and a second marker portion is fixedly provided in a second portion of the main body that is located in rear of the second inclined surface as seen in the direction in which the main body is inserted in the tubular organ, and on said other side of the center axis line on which side the second lumen is formed, and wherein the first and second portions of the main body are remote from each other in the axial direction.

19. The catheter according to claim 1, wherein a front end portion of the main body is a diagonal pair of inclined surfaces.

20. The catheter according to claim 1, wherein a length of the second lumen is equal to or longer than a length of the first lumen.

21. The catheter according to claim 12, wherein a front end portion of the main body is a diagonal pair of inclined surfaces.

22. The catheter according to claim 12, wherein a length of the second lumen is equal to or longer than a length of the first lumen.

* * * * *